US009215999B2

(12) United States Patent
Richardson et al.

(10) Patent No.: US 9,215,999 B2
(45) Date of Patent: Dec. 22, 2015

(54) EEG MONITOR OF FETAL HEALTH

(75) Inventors: Bryan S. Richardson, London (CA); Martin G. Frasch, London (CA)

(73) Assignee: The London Health Sciences Centre Research Inc., London, Ontario (CA)

(*) Notice: Subject to any disclaimer, the term of this patent is extended or adjusted under 35 U.S.C. 154(b) by 1437 days.

(21) Appl. No.: 12/532,874

(22) PCT Filed: Mar. 28, 2008

(86) PCT No.: PCT/CA2008/000580
§ 371 (c)(1),
(2), (4) Date: Nov. 8, 2010

(87) PCT Pub. No.: WO2008/116317
PCT Pub. Date: Oct. 2, 2008

(65) Prior Publication Data
US 2011/0152633 A1 Jun. 23, 2011

Related U.S. Application Data

(60) Provisional application No. 60/908,587, filed on Mar. 28, 2007.

(51) Int. Cl.
A61B 5/048 (2006.01)
A61B 5/00 (2006.01)
A61B 5/024 (2006.01)
(Continued)

(52) U.S. Cl.
CPC ........... *A61B 5/7246* (2013.01); *A61B 5/02411* (2013.01); *A61B 5/048* (2013.01); *A61B 5/4362* (2013.01); *B63B 29/06* (2013.01); *B63C 11/02* (2013.01); *F16M 11/24* (2013.01); *F16M 13/02* (2013.01); *A61B 5/0448* (2013.01); *A61B 5/7257* (2013.01); *B63C 2011/024* (2013.01)

(58) Field of Classification Search
CPC .... A61B 5/04; A61B 5/04012; A61B 5/0444; A61B 5/0476; A61B 5/048; A61B 5/4343; A61B 5/4362; A61B 5/024; A61B 5/02411; A61B 5/0448; A61B 5/7257; A61B 5/7275
USPC .......................... 600/500–507, 509, 544, 545
See application file for complete search history.

(56) References Cited

U.S. PATENT DOCUMENTS 4,951,680 A     8/1990  Kirk et al.
5,029,082 A *   7/1991  Shen et al. ............... 600/512
(Continued)

OTHER PUBLICATIONS

Thaler et al. "Real-time spectral analysis of the fetal EEG: a new approach to monitoring sleep states and fetal condition during labor." Pediatr Res. Sep. 2000;48(3):340-5.*

(Continued)

*Primary Examiner* — Navin Natnithithadha
*Assistant Examiner* — Meredith Weare
(74) *Attorney, Agent, or Firm* — Bereskin & Parr LLP

(57) ABSTRACT

A method for predicting health compromise in a fetus comprises acquiring one or more EEG signals and a fetal heart rate (FHR) signal from the surface of the head of a fetus; and determining the spectral edge frequency (SEF) of the one or more EEG signals. A repetitive temporal correlation between the FHR signal and the SEF of the one or more EEG signals is indicative of fetal health compromise. A system for detecting the correlation between FHR signal and the SEF of the one or more EEG signals and predicting fetal health compromise is also described.

17 Claims, 6 Drawing Sheets

(51) Int. Cl.
  *B63B 29/06* (2006.01)
  *B63C 11/02* (2006.01)
  *F16M 11/24* (2006.01)
  *F16M 13/02* (2006.01)
  *A61B 5/0448* (2006.01)

(56) References Cited

U.S. PATENT DOCUMENTS

| | | | |
|---|---|---|---|
| 5,206,807 | A | 4/1993 | Hatke et al. |
| 5,425,362 | A * | 6/1995 | Siker et al. ............... 600/376 |
| 5,957,855 | A | 9/1999 | Oriol et al. |
| 6,024,701 | A | 2/2000 | Almog |
| 6,493,577 | B1 | 12/2002 | Williams |
| 6,556,861 | B1 | 4/2003 | Prichep |
| 7,047,055 | B2 | 5/2006 | Boas et al. |
| 2002/0193670 | A1 * | 12/2002 | Garfield et al. ............... 600/304 |
| 2004/0082842 | A1 | 4/2004 | Lumba et al. |

OTHER PUBLICATIONS

Jensen et al. "Dynamics of fetal circulatory responses to hypoxia and asphyxia." Eur J Obstet Gynecol Reprod Biol. Jun. 1999;84(2):155-72.*

Klink et al. "Alterations of the fetal EEG under the influence of labour, hypoxia and analgetics." J Perinat Med. 1981;9 Suppl 1:131-2.*

West, Claire Richardyne. The role of spectral edge frequency monitoring in neonatal intensive care. The University of Auckland. 2006. 245 pages.*

Bloom et al., Fetal Pulse Oximetry and Cesarean Delivery, The New England Journal of Medicine, vol. 355:2195-2202, Nov. 23, 2006, Downloaded from nejm.org on May 9, 2007.

* cited by examiner

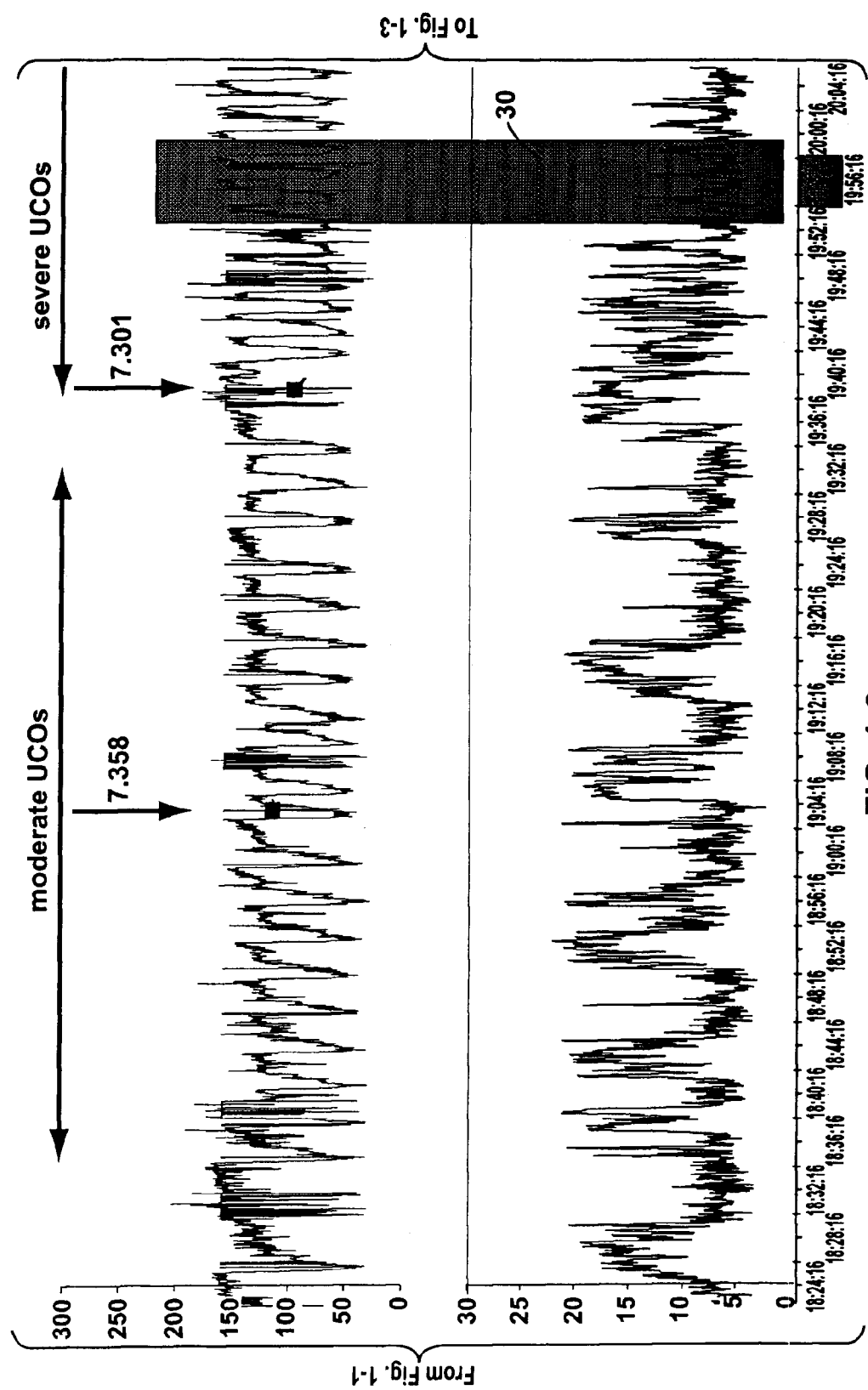

EEG MONITOR OF FETAL HEALTH

FIELD

Various aspects of the present invention relate to methods and systems to monitor and detect early changes of fetal electroencephalogram (EEG) activity due to asphyxia during labour. More particularly, various aspects of the present invention relate to methods and systems to predict fetal health compromise due to asphyxia during labour.

BACKGROUND

Uterine contractions during labour can restrict maternal uterine and/or fetal umbilical blood flow compromising fetal oxygenation and leading to fetal hypoxia/acidosis. Fetal monitors of various types are widely used in the obstetrics field.

Fetal heart rate (FHR) monitoring is widely used during labour and FHR decelerations predict hypoxic change. Numerous studies using electro-cardiogram (ECG) and FHR have been published. Intrapartum fetal ECG readings are obtained through the scalp electrodes. A drawback of the various types of fetal monitors currently used in obstetrics is that they provide for poor positive predictive value for fetal acidosis. After many caesarian deliveries performed on the basis of FHR information using these conventional techniques, it has been found that the fetus was not really in critical distress.

Monitoring of oxygen saturation can allow direct assessment of both fetal oxygen status and fetal tissue perfusion. Pulse oximetry, a subclass of the general field of oximetry, uses changes in arterial blood volume through a heart beat cycle to internally calibrate oxygen saturation measurements. However, knowledge of fetal oxygen saturation does not appear to lower the rate of unnecessary caesarean sections or improve infant health (Bloom et al., New England Volume 355:2195-2202).

SUMMARY

In one aspect, at least one embodiment described herein provides a method for monitoring fetal health compromise due to fetal hypoxia/asphyxia, comprising (a) acquiring one or more electroencephalogram (EEG) signals from the surface of the head of a fetus in a form suitable to identify patterns in the one or more EEG signals, (b) acquiring a Fetal Heart Rate (FHR) signal in a form suitable to identify patterns in the FHR signal, and (c) predicting the fetal health compromise based on a repetitive temporal correlation between the patterns in the FHR signal and the patterns in the one or more EEG signals.

In another aspect, at least one embodiment described herein provides a system for monitoring fetal health compromise due to fetal hypoxia/asphyxia, comprising: (a) means for acquiring one or more electroencephalogram (EEG) signals from the surface of the head of the fetus in a form suitable to identify patterns in the EEG, (b) means for determining a Fetal Heart Rate (FHR) signal in a form suitable to identify patterns in the FHR signal, and (c) means to compare a repetitive temporal correlation between the patterns of the EEG and the patterns of the FHR signal.

In another aspect, at least one embodiment described herein provides a method of monitoring fetal health comprising acquiring one or more electrophysiological signals from a cranial region of a fetus; determining a Fetal Heart Rate (FHR) signal; performing correlation based on the one or more EEG signals and the FHR signal; and analyzing the correlation to detect fetal health compromise.

In another aspect, at least one embodiment described herein provides a system for monitoring fetal health comprising: a control unit for controlling the system; a data acquisition unit connectable to sensors coupled to a cranial region of the fetus, the data acquisition unit being configured by the control unit to acquire one or more electrophysiological signals from the cranial region of the fetus; and a signal processing unit configured to perform correlation based on the one or more electrophysiological signals and a Fetal Heart Rate (FHR) signal and analyze the correlation to detect fetal health compromise.

In another aspect, at least one embodiment described herein provides a use of a system for monitoring fetal health. The system comprises: a control unit for controlling the system; a data acquisition unit connectable to sensors coupled to a cranial region of the fetus, the data acquisition unit being configured by the control unit to acquire one or more electrophysiological signals from the cranial region of the fetus; and a signal processing unit configured to perform correlation based on the one or more EEG signals and a Fetal Heart Rate (FHR) signal and analyze the correlation to detect fetal health compromise.

BRIEF DESCRIPTION OF THE DRAWINGS

For a better understanding of various exemplary embodiments described herein and to show more clearly how they may be carried into effect, reference will now be made, by way of example only, to the accompanying drawings which show at least one exemplary embodiment and in which.

DETAILED DESCRIPTION

Figure 1:
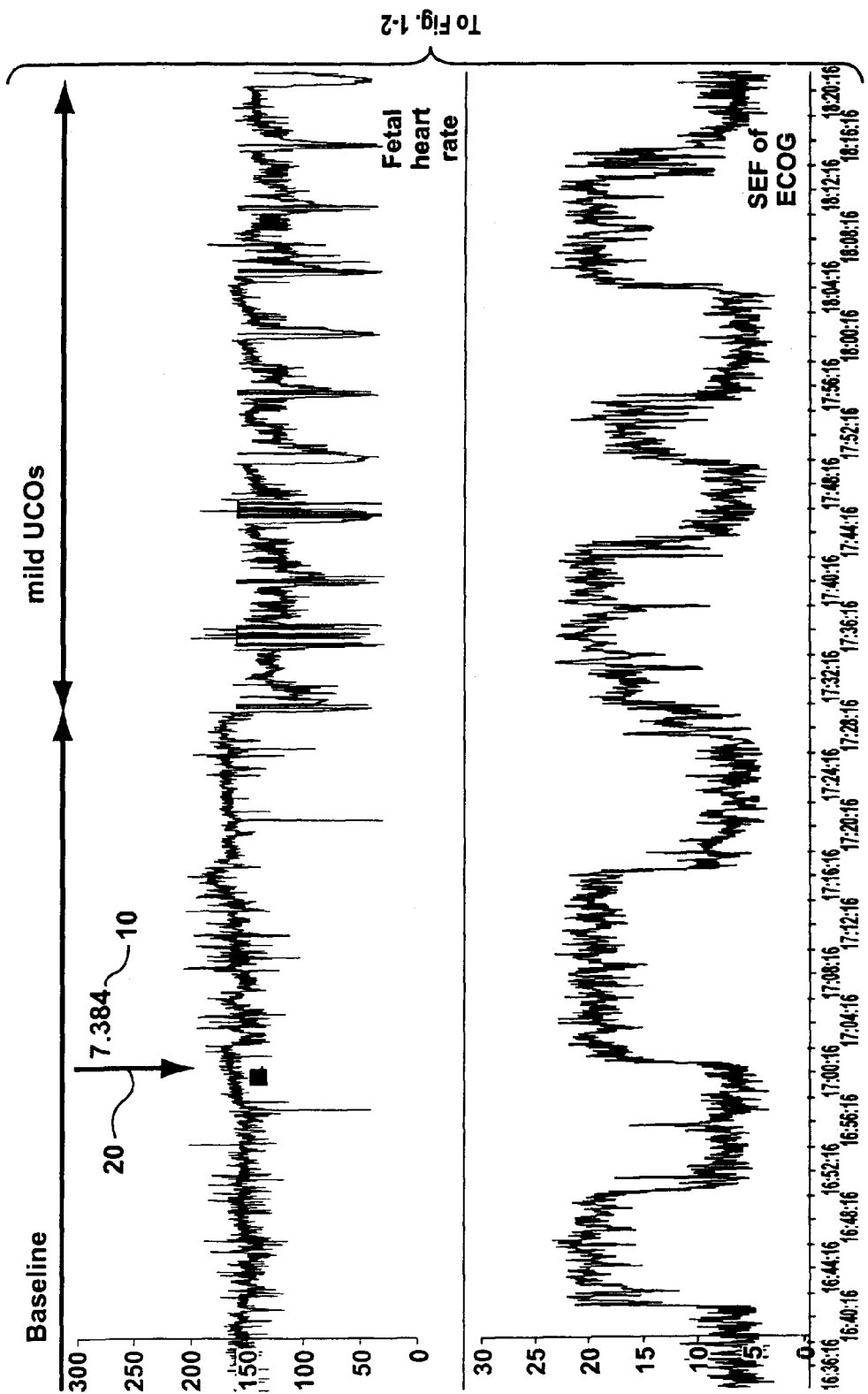
FIG. 1 shows several graphs of heart rate and spectral edge frequency of electrocorticogram (ECoG) for an ovine fetus during three series of umbilical cord occlusions of increasing severity.

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the embodiments of the invention described herein. Some features in the figures have not been drawn to scale. Further, it should be understood by those of ordinary skill in the art that the embodiments described herein may be practiced without these specific details. In other instances, well-known methods, procedures and components have not been described in detail so as not to obscure the embodiments described herein. Furthermore, this description should not be considered as limiting the scope of the embodiments described herein, but rather as merely describing the implementation of the various embodiments described herein.

Various embodiments are described herein of methods and systems that are useful for the monitoring of fetal health for fetal hypoxia/asphyxia and/or acidosis. The methods and systems of monitoring described herein comprise electrophysiological (EEG) and fetal heart rate (FHR) analysis using a technique that provides a predictive value for the early prediction of fetal cerebral compromise due to fetal hypoxia/asphyxia with worsening acidosis.

The methods described herein are based on a temporal correlation between EEG and FHR. However, signals other than the EEG may be used. In at least one embodiment, a power spectral analysis of the EEG is used by employing spectral edge frequency analysis (SEF). The methods are based on pathophysiological mechanisms occurring during worsening acidosis.

The methods and systems described herein for predicting fetal health compromise were developed in the near term ovine fetus with repetitive cord occlusions (UCO) as might be seen during labour and leading to fetal hypoxia/acidosis and are extendable to the application of fetal health monitoring for human fetuses.

The methods and systems described herein can be used to predict fetal acidosis reliably and at its early onset. It can be used as an objective, observer independent, online measure of fetal brain function, and to respond to hypoxemia with worsening acidosis.

In one exemplary embodiment, a method for the early prediction of fetal health compromises due to fetal hypoxia/asphyxia comprises measuring a power spectral analysis of electrocortical activity called spectral edge frequency (SEF) analysis that determines the frequency under which a certain percentage of all spectral power of EEG in a certain interval is contained such as 95% of all EEG spectral power in an interval of 4 seconds for example. This is done in a sliding window over the course of the fetal monitoring period along with fetal heart rate (FHR) monitoring. When FHR decelerations become highly correlated with time course of SEF, it has been found that this moment signifies a fetal condition 52±34 min prior to a sudden drop of fetal pH to a value of less than about 7.0.

The SEF is one way to visualize and quantify the EEG patterns. It is also a well established one. However, there are other methods of visualizing and quantifying the EEG patterns. One such method includes the so-called envelope function of the EEG. Accordingly, it should be understood that any appropriate method of EEG analysis that results in a signal that can be then correlated to FHR patterns to detect fetal health compromise can be used. The analysis can for example be performed in the frequency domain as well as other domains, including but not limited to, in EEG complexity domains or as continuous Granger causality EEG/FHR analysis.

FIG. 1 shows a representative time course of a complete experiment. Specifically, FIG. 1 shows aligned plots of fetal heart rate (FHR) and the Spectral Edge Frequency of ECoG (Electrocorticogram). Also shown in FIG. 1 are the corresponding pH values 10 with arrows 20 indicating the points of pH sampling. As can be seen from the figure there are three series of umbilical cord occlusions (UCOs) with temporal correlation indicated by 30. The time of onset is approximately 8 pm and the time at which the pH drops to a value of less than 7.0 is approximately 9 pm.

Figures 1, 2, 3:
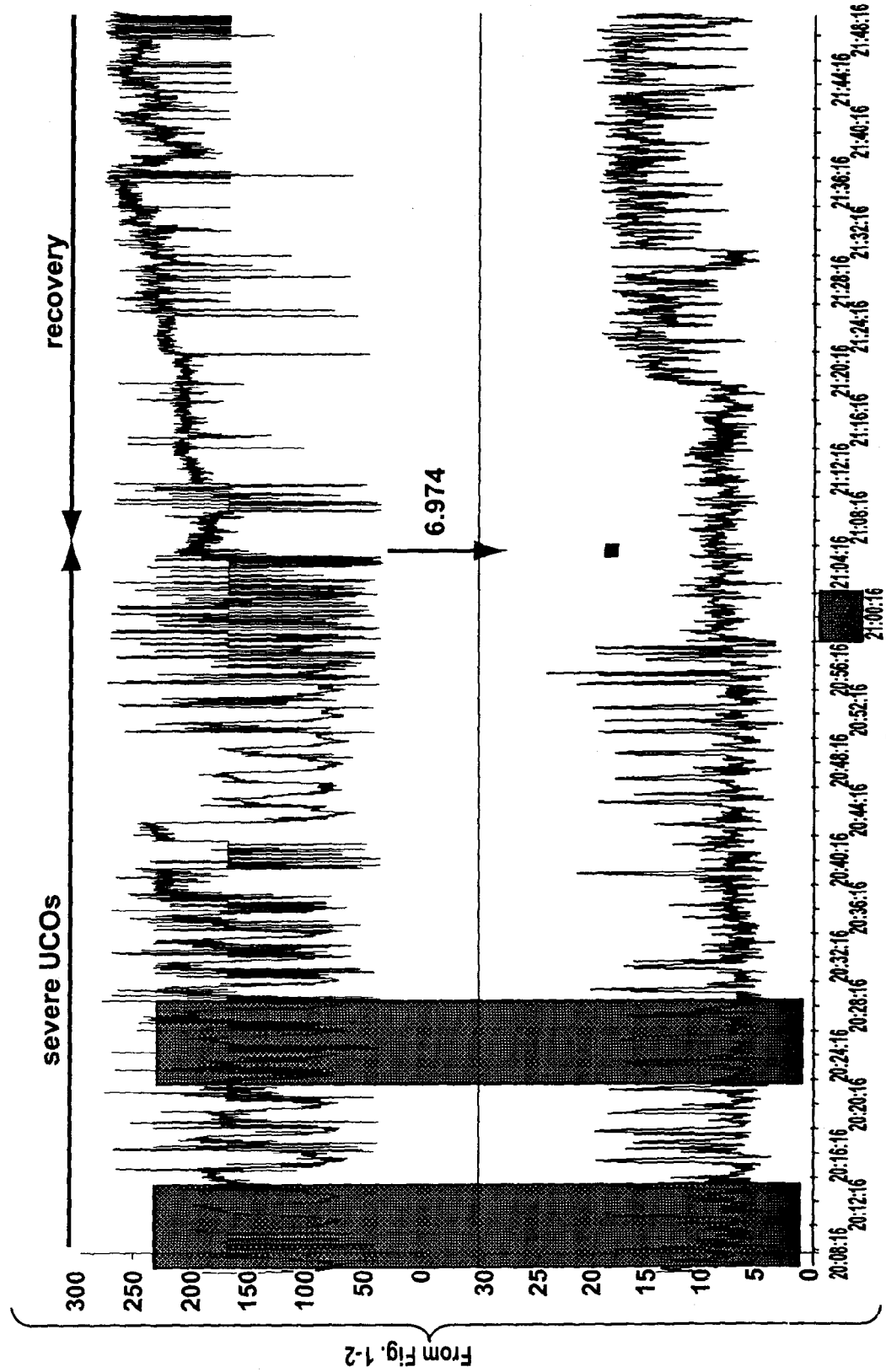
FIG. 2 shows several graphs of arterial blood pressure, heart rate, ECoG and spectral edge frequency of ECoG recordings for ovine fetus during a series of umbilical cord occlusions.
FIG. 3 is a graph comparing the temporal correlation of the spectral edge frequency of ECoG and the fetal heart rate during moderate and severe umbilical cord occlusions in ovine fetus expressed as R values of regression.
Figure 2:
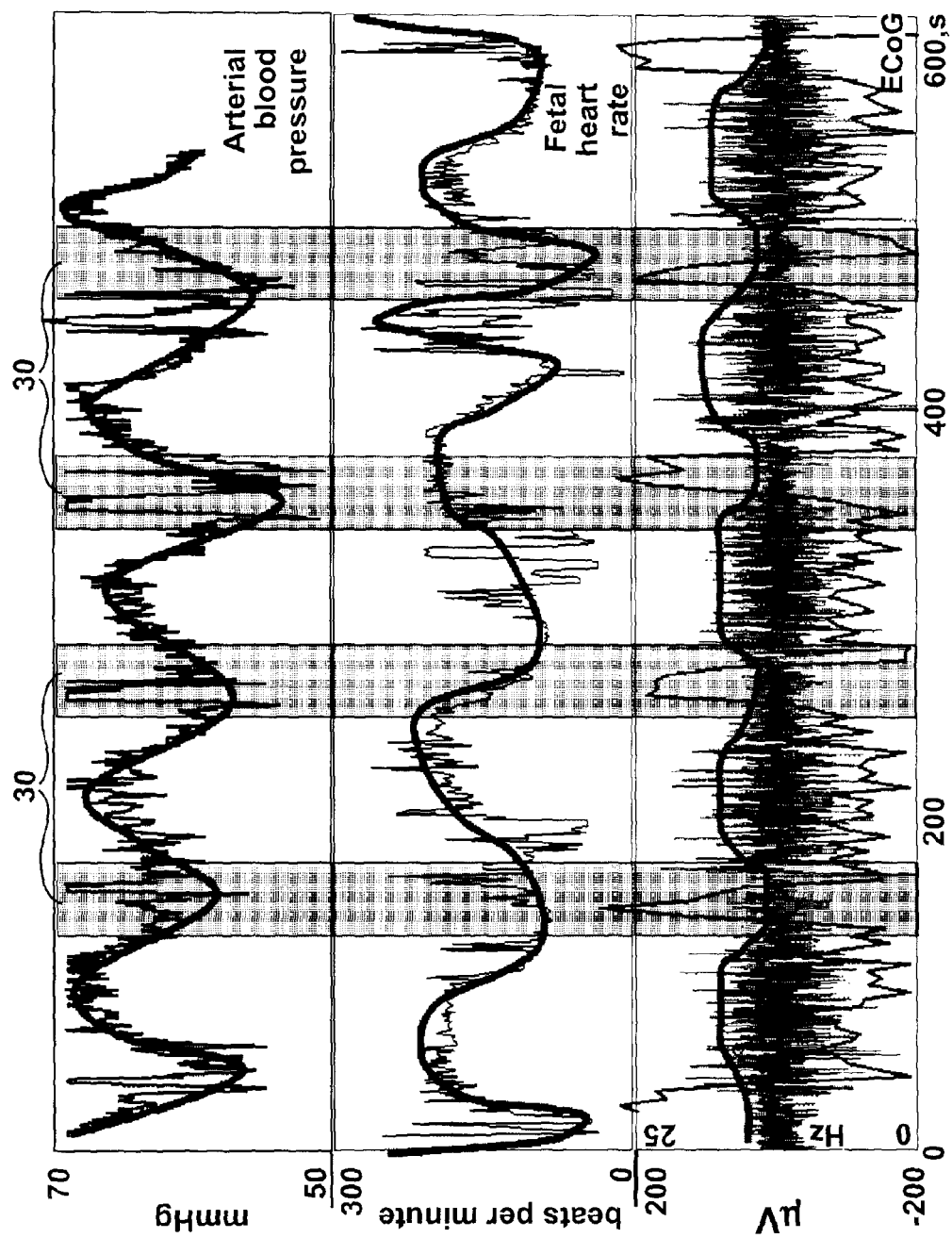
Figure 3:
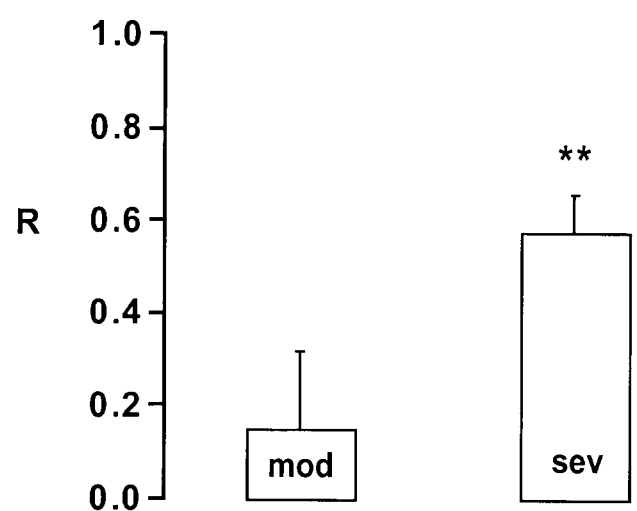

FIG. 2 shows a demonstration of the typical temporal correlation 30 of arterial blood pressure, fetal heart rate, ECoG and Spectral Edge Frequency of ECoG during a series of severe UCOs at about 30 minutes before a pH of less than 7.0 is reached.

In one embodiment, the correlation can be monitored by continuous calculation of one of the measures reflecting this pathophysiological phenomenon. For example, this can be achieved by determining the maximum of cross-correlation function of SEF and FHR. Alternatively, this can be achieved by determining the correlation of the FHR and SEF of the ECoG correlation expressed as R values of regression of subsequent time interval differences between SEF maxima and FHR minima (i.e. degree of "synchronization" between SEF ECoG and FHR).

FIG. 3 shows the correlation of the FHR with the SEF of the ECoG expressed as R values of regression of subsequent time interval differences between SEF maxima and FHR minima (i.e. the degree of "synchronization" between SEF ECoG and FHR). FIG. 3 illustrates the correlation during moderate (mod) and severe (sev) UCOs. Specifically, the following parameters were used: time interval differences between SEF maxima correlated to the time interval differences between the corresponding FHR minima, sample size N=7. Significance level marked as ** for p value <0.001 versus moderate occlusion series (i.e., statistical significance level of the difference between moderate and severe UCO series is less than 0.001 determined using Wilcoxon test). Of note, R increases in each individual case.

During moderate occlusions, i.e., there is a relatively low degree of fetal acidosis, no significant SEF ECoG—FHR correlation pattern is observed. This is expressed in low correlation (low R value). During the severe occlusions the correlation increases due to the underlying pathophysiological alterations in ECoG leading to the SEF ECoG pattern "cycling" nearly synchronically with FHR decelerations induced by the occlusions. This change was observed 52±34 min prior to a pH drop below 7.0. Thus, it could be used to predict such a pH drop, i.e. critical fetal acidosis.

A method to detect fetal health compromise includes: 1) detecting SEF high frequency peaks above a first frequency, at a set time interval apart, decreasing under a second frequency in between the peaks as long as a series of at least two consecutive peaks can be found as defined above; 2) detecting the minima of FHR decelerations; 3) determining times of the events in steps 1 and 2; and 4) calculating time differences between the subsequent SEF peaks and FHR minima, respectively. These time differences are then subjected to analysis to monitor fetal health.

For example, in various embodiments, the increase of the correlation of the subsequent time intervals of SEF EEG maxima and FHR minima is used to identify fetal health compromise. The specific values for individual species may be obtained by routine calibration tests. For example, in some embodiments, based on the experiments in ovine fetus the first frequency is 13 Hz, the set time interval is 90 seconds, and the second frequency is 7 Hz. These values may differ for human fetuses.

EXAMPLES

The examples are described for the purposes of illustration and are not intended to limit the scope of the invention. Near-term ovine fetuses (N=7, 125±2 days of gestation (dGA), term 145 dGA) underwent chronic preparation with fetal brachial artery catheters, electrocardiogram (ECG), biparietal ECoG electrodes and placement of an inflatable umbilical cord occluder. Fetal heart rate was determined by detecting R peaks of ECG. Following a minimum 3 days recovery from surgery, fetuses underwent a series of mild (1 min duration-5 min apart), moderate (1 min-3 min) and severe (1 min-2 min) UCO each lasting 1 hr or until fetal arterial pH decreased to 7.0. Fetal arterial blood samples were drawn at baseline, immediately before and during the first mild, moderate and severe UCO and at 20 min intervals during the moderate and severe UCOs. Whenever the targeted pH value of less than 7.0 was detected, the UCO series were terminated.

Repetitive UCOs led to development of a marked acidosis (pH 7.36±0.03 to 6.91±0.12, P<0.001; base deficit (BD) −3.7±1.7 to 16.4±2.5 mmol/l, P<0.001). At 52±34 min prior to a pH drop to less than 7.0, the SEF of ECoG increased up to 23±2 Hz from 3±1 Hz during each deceleration (p <0.001) and was correlated to FHR decelerations (as can be seen in each of FIGS. 1, 2, and 3) as well as the pathological decreases of fetal ABP during each FHR deceleration (FIG. 2).

Figure 4:
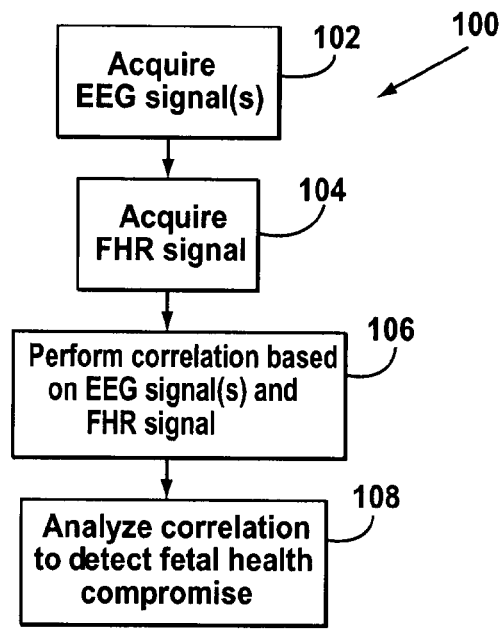
FIG. 4 is a flow chart diagram of an exemplary embodiment of a method for monitoring fetal health compromises; and, FIG. 5 is a block diagram of an exemplary system for monitoring fetal health compromise.

Referring now to FIG. 4, shown therein is a flowchart showing an exemplary embodiment of a method 100 for detecting fetal health compromise. At step 102, at least one EEG signal is obtained from the fetus. In other embodiments, at step 102, at least one ECoG signal can be obtained from the fetus. At step 104, an FHR signal is obtained. In some embodiments, the FHR signal can be obtained directly from the fetus in which case steps 102 and 104 are done simultaneously. In some other embodiments, the FHR signal can be derived from the EEG signal. At step 106, a correlation is performed based on the EEG signal(s) and the FHR signal using techniques described herein. The correlation can be based on processed versions of the EEG signal(s) and the FHR signal in which signal processing is done that shows related patterns in the EEG signal(s) and the FHR signal. This can be done by correlation analysis showing similarities in the patterns in the EEG signal(s) and the FHR signal. The correlation can be a temporal correlation or Granger causality index or indices derived from bivariate (EEG and FHR signals) analysis in complexity domain, for example, from the general mutual information function. The correlation may be done to correlate FHR decelerations with the EEG. In at least some implementations, the EEG signal(s) can be processed to obtain the SEF and the FHR decelerations (i.e. minima) can be correlated with the peaks (i.e. maxima) of the SEF.

At step 108, the correlation is analyzed to determine if there is a potential fetal health compromise that is occurring or is likely to occur. This analysis includes determining whether the correlation indicates a similarity in information contained in the EEG signal(s) and the FHR signal. For example, this analysis can include applying a previously empirically determined threshold to the correlation results expressed as R values of the correlation of time intervals between SEF EEG maxima and corresponding FHR minima. Alternatively, this analysis can also be done in a visual manner by placing the processed signals on top of one another as in FIG. 1 and determining if there is a correlation. Alternatively, this can be done by calculating the R value to show the statistical correlation between the minima and maxima mentioned above and comparing it to a threshold. For example, in some embodiments, if the R value is above 0.5, then step 108 determines that there is a good evidence that the fetus is experiencing acidosis.

Figure 5:
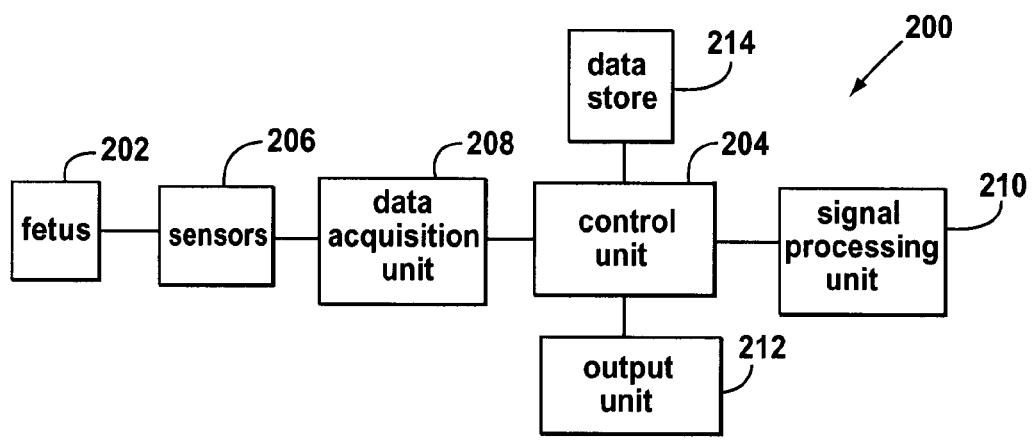

Referring now to FIG. 5, shown therein is a block diagram of an exemplary embodiment of a fetal heath monitoring system 200 for monitoring the health of a fetus 202. The fetal health monitoring system 200 includes a control unit 204, sensors 206, a data acquisition unit 208, a signal processing unit 210, an output unit 212 and a data store 214. In some cases, one or more of these blocks may be optional.

The control unit 204 controls the operation of the system 200 and directs the activity of acquiring data from the fetus 202 during fetal health monitoring, and processing this data to determine if fetal heath compromise is occurring or will occur. Once the sensors 206 have been placed on the fetus 202 to record EEG and ECG (to determine FHR), the control unit 204 configures the data acquisition unit 208 to acquire data from the sensors 206. The data that is acquired can include one or more EEG signals from the fetus 202. In other cases, the data that is acquired can include one or more ECoG signals from the fetus. Accordingly, in these instances the sensors 206 include electrodes. In some embodiments, an FHR signal can also be acquired from the fetus 202. As used herein, "acquiring an FHR signal" may refer to either directly measuring the FHR signal from the fetus or deriving the FHR signal from another signal. In embodiments in which the FHR signal is directly measured, the sensors 206 include appropriate transducers for acquiring such information. Alternatively, in various other embodiments, the FHR signal may be derived from the ECG signal(s) by the signal processing unit 210. The data acquisition unit 208 includes circuitry for receiving signals from the sensors 206, preprocessing these signals and digitizing the preprocessed signals as is commonly known to those skilled in the art. Accordingly, the data acquisition unit 208 typically includes amplification and filtering circuitry as well as an analog to digital converter.

The control unit 204 then directs the acquired data to the signal processing unit 210 which implements one or more of the techniques described above. Depending on the particular implementation, this can include performing spectral analysis to obtain the SEF of the EEG signal(s) or obtaining the envelope of the EEG signal(s) and then performing the correlation between the processed EEG signal(s) and the FHR signal. In some embodiments, other processing steps may also be performed as described above. The results of the analysis can then be displayed by the output unit 212, or the processed signals can be displayed by the output unit 212 for visual analysis. One or more of the acquired data, processed signals and analysis results can also be stored on the data store 214.

In one implementation, the control unit 204, the signal processing unit 210, the output unit 212 and the data store 214 can be provided by a desktop computer, laptop computer, or any other appropriate computing device (not shown). In this case, the processor of the computing device can implement the functionality of the control unit 204 and the signal processing unit 204, the output unit 212 can be the display of the computing device, and the data store 214 can be the memory of the computing device. In some embodiments, the output unit 212 can be a printer and the data store 214 can be a server to which the computing device can be connected.

In one aspect, at least one embodiment described herein provides a method for monitoring fetal health compromise due to fetal hypoxia/asphyxia, comprising (a) acquiring one or more electroencephalogram (EEG) signals from the surface of the head of a fetus in a form suitable to identify patterns in the one or more EEG signals; (b) acquiring a Fetal Heart Rate (FHR) signal in a form suitable to identify patterns in the FHR signal; and (c) predicting the fetal health compromise based on a repetitive temporal correlation between the patterns in the FHR signal and the patterns in the one or more EEG signals.

In one aspect, the method further includes performing an analysis of the one or more EEG signals to identify patterns in the EEG.

In another aspect, the analysis is one of a spectral edge frequency (SEF) of the one or more EEG signals and an envelope function of the one or more EEG signals.

In another aspect, the analysis is a spectral edge frequency (SEF) of the one or more EEG signals.

In another aspect of the method, the patterns in the FHR signal comprise minima of the FHR signal, and the patterns in the one or more EEG signals comprise maxima of the SEF, wherein the minima comprise nadirs of the FHR deceleration and the maxima comprise peaks of the SEF.

In another aspect, the method may further include: (d) determining minima of the FHR signal and first time intervals between said minima; (e) determining maxima of the SEF of the one or more EEG signals and second time intervals between said maxima; and (f) determining a correlation value between the first and second time intervals.

In a further aspect of the method, a correlation value above 0.4 is indicative of fetal health compromise.

In a further aspect of the method, a correlation value above 0.5 is indicative of fetal health compromise.

In another aspect of the method, the SEF of the one or more EEG signals is determined in a frequency domain below 40 Hz.

In another aspect, the SEF of the one or more EEG signals is determined in a frequency domain below 30 Hz.

In another aspect, the method may further include determining the frequency below which about 90% of the EEG activity occurs.

In another aspect, the method may further include determining the frequency below which about 95% of the EEG activity occurs.

In a further aspect of the method, the one or more EEG signals are acquired from one or more electrodes placed on the fetus' head over the parasagittal region/fronto-parietal-occipital cortex.

In another aspect of the method, the fetal health compromise is predicted between 15 and 90 minutes prior to a drop in fetal pH under 7.0.

In another aspect of the method, the method includes monitoring for fetal health compromise in which fetal acidosis occurs. Alternatively, or in addition to, the method can include monitoring for fetal health compromise in which a cerebral fetal compromise occurs.

Another aspect of the method includes applying to the fetus a therapy to guard against the further development of acidosis after the FHR becomes temporally correlated with the SEF. In one aspect, the therapy can include expediting the delivery of the fetus. In some embodiments of the method this can include but is not limited to delivering the fetus through caesarean section.

In another aspect of the method, the FHR signal is derived from an electro-cardiogram (ECG) signal.

In yet another aspect of the method, the EEG signal is an Electrocorticogram (ECoG) signal.

In yet a further aspect of the method, the fetus is a human fetus.

In another aspect, at least one embodiment described herein provides a system for monitoring fetal health compromise due to fetal hypoxia/asphyxia, comprising: (a) means for acquiring one or more electroencephalogram (EEG) signals from the surface of the head of the fetus in a form suitable to identify patterns in the EEG, (b) means for determining a Fetal Heart Rate (FHR) signal in a form suitable to identify patterns in the FHR, and (c) means to compare a repetitive temporal correlation between the patterns of the EEG and the patterns of the FHR signal.

The system may further include means for performing an analysis of the one or more EEG signals in a form suitable to identify patterns in the one or more EEG signals.

In another aspect, the system may further include means for determining the time intervals between the FHR patterns and means for determining the time intervals between the EEG patterns.

In yet another aspect, the system may further include means for determining a correlation value between the time intervals of the FHR patterns and the time intervals of the EEG patterns.

In another aspect of the system, the EEG analysis may be done using one of spectral edge frequency (SEF) of the one or more EEG signals and an envelope function of the one or more EEG signals.

In yet another aspect of the system, the FHR patterns comprise the minima of the FHR signal. In another aspect of the system the EEG patterns comprise the maxima of the SEF.

In another aspect, at least one embodiment described herein provides a method of monitoring fetal health comprising: acquiring one or more electrical signals from a cranial region of a fetus; determining a Fetal Heart Rate (FHR) signal; performing correlation based on the one or more electrical signals and the FHR signal; and analyzing the correlation to detect fetal health compromise.

In another aspect, the method comprises determining the FHR signal by one of: acquiring data from the fetus and deriving the FHR signal from one or more electrical signals.

In another aspect, at least one embodiment described herein provides a system for monitoring fetal health comprising: a control unit for controlling the system; a data acquisition unit connectable to sensors coupled to a cranial region of the fetus, the data acquisition unit being configured by the control unit to acquire one or more electrical signals from the cranial region of the fetus; and a signal processing unit configured to perform correlation based on the one or more electrical signals and a Fetal Heart Rate (FHR) signal and analyze the correlation to detect fetal health compromise.

In another aspect, the system is configured to determine the FHR signal by one of: acquiring data from the fetus and deriving the FHR signal from the one or more electrical signals.

In another aspect, at least one embodiment described herein provides a use of a system for monitoring fetal health. The system comprises: a control unit for controlling the system; a data acquisition unit connectable to sensors coupled to a cranial region of the fetus, the data acquisition unit being configured by the control unit to acquire one or more electrical signals from the cranial region of the fetus; and a signal processing unit configured to perform correlation based on the one or more electrical signals and a Fetal Heart Rate (FHR) signal and analyze the correlation to detect fetal health compromise.

In various embodiments, a single electrophysiological signal (such as an EEG signal) may be acquired from the fetus. In various other embodiments, a plurality of electrophysiological signals may be acquired from the fetus. In some such embodiments, a single electrophysiological signal may be selected from the plurality of signals in any appropriate manner. For example, but not limited to, the signal may be selected based on signal to noise ratio (SNR), signal amplitude or any other appropriate measure of signal quality. In some other embodiments, all or some of the plurality of signals may be averaged in any appropriate manner to for example obtain an improved signal quality. The signal quality may be determined by any appropriate measure including but not limited to SNR. In each of these cases, the resulting electrophysiological signal can be used in the analysis.

It should be understood that various modifications can be made to the embodiments described and illustrated herein, The embodiments of the invention in which an exclusive property or privilege is claimed are defined as follows:

1. A method for the early prediction of fetal health compromise due to fetal hypoxia/asphyxia, comprising:
   (a) acquiring and identifying patterns in a Fetal Heart Rate (FHR) signal, wherein identifying patterns in the FHR signal comprises determining minima of the FHR signal and first time intervals between said minima;
   (b) acquiring one or more electroencephalogram (EEG) signals from at least one sensor placed on the surface of the head of a fetus and identifying patterns in the one or more EEG signals by performing an analysis based on a spectral edge frequency (SEF) of the one or more EEG signals, wherein identifying patterns in the one or more EEG signals comprises determining maxima of the SEF of the one or more EEG signals and second time intervals between said maxima;
   (c) determining a repetitive temporal correlation between the patterns in the FHR signal and the patterns in the one or more EEG signal by determining a correlation value between the first time intervals and the second time intervals; and
   (d) predicting the fetal health compromise based on the repetitive temporal correlation.

2. The method of claim 1, wherein the minima of the FHR signal comprise nadirs of FHR deceleration and the maxima of the SEF of the one or more EEG signals comprise peaks of the SEF.

3. The method of claim 1, wherein the correlation value is indicative of fetal health compromise when the correlation value is above 0.4.

4. The method of claim 1, wherein the correlation value is indicative of fetal health compromise when the correlation value is above 0.5.

5. The method of claim 1, wherein the SEF of the one or more EEG signals is determined in a frequency domain below 40 Hz.

6. The method of claim 1, wherein the SEF of the one or more EEG signals is determined in a frequency domain below 30 Hz.

7. The method of claim 1, wherein performing the analysis based on SEF of the one or more EEG signals comprises determining the frequency below which about 90% of the EEG activity occurs.

8. The method of claim 1, wherein performing the analysis based on SEF of the one or more EEG signals comprises determining the frequency below which about 95% of the EEG activity occurs.

9. The method of claim 1, wherein the one or more EEG signals are acquired from one or more electrodes placed on the fetus' head over the parasagittal region/fronto-parietal-occipital cortex.

10. The method of claim 1, wherein the fetal health compromise is fetal acidosis.

11. The method of claim 1, wherein the fetal health compromise is a cerebral fetal compromise.

12. The method of claim 1, further comprising applying to the fetus a therapy against development of acidosis after the FHR minima becomes temporally correlated with the maxima of the SEF.

13. The method of claim 12, wherein the therapy is expediting the delivery of the fetus.

14. The method of claim 1, wherein the FHR signal is derived from an electro-cardiogram (ECG) signal.

15. The method of claim 1, wherein the one or more EEG signals is an Electrocorticogram (ECoG) signal.

16. The method of claim 1, wherein the fetus is a human fetus.

17. A system for the early prediction of fetal health compromise due to fetal hypoxia/asphyxia, comprising:
   (a) means for acquiring and determining patterns in a Fetal Heart Rate (FHR) signal including means for determining minima of the FHR signal and first time intervals between said minima;
   (b) means for acquiring and identifying patterns in one or more electroencephalogram (EEG) signals from the surface of the head of the fetus by analyzing one of a spectral edge frequency (SEF) pattern comprising a maxima of the SEF of the one or more EEG signals and an envelope function of the one or more EEG signals including means for determining maxima of the SEF of the one or more EEG signals and second time intervals between said maxima;
   (c) means for determining a repetitive temporal correlation between the patterns in the FHR signal and the patterns in the one or more EEG signal by determining a correlation value between the first time intervals and the second time intervals; and
   (d) means for predicting the fetal health compromise based on the repetitive temporal correlation.

* * * * *